United States Patent [19]

Miyoshi et al.

[11] Patent Number: 4,863,800

[45] Date of Patent: Sep. 5, 1989

[54] SURFACE-TREATED PIGMENT MATERIAL

[75] Inventors: Ryota Miyoshi, Yono; Isao Imai, Kuki, both of Japan

[73] Assignee: Miyoshi Kasei Co., Ltd., Urawa, Japan

[21] Appl. No.: 22,693

[22] Filed: Mar. 6, 1987

[51] Int. Cl.$^4$ .................. C04B 14/00; C09C 1/00; A61K 7/035

[52] U.S. Cl. ...................... 428/403; 106/23; 106/27; 106/262; 106/507; 424/69; 428/404; 428/405; 428/407

[58] Field of Search ............. 428/403, 405; 106/262, 106/308 F, 23, 27, 504; 424/69

[56] References Cited

U.S. PATENT DOCUMENTS

| | | | |
|---|---|---|---|
| 3,592,940 | 7/1981 | Quesada | 424/69 |
| 4,126,593 | 11/1978 | Takahashi | 524/425 |
| 4,606,914 | 8/1986 | Miyoshi | 424/63 |
| 4,622,074 | 11/1986 | Miyoshi et al. | 106/308 |
| 4,627,876 | 12/1986 | Fries et al. | 106/27 |
| 4,648,908 | 3/1987 | Takasuka et al. | 106/308 F |

FOREIGN PATENT DOCUMENTS 55-136213  10/1980  Japan.
56-29512   3/1981   Japan.

Primary Examiner—George F. Lesmes
Assistant Examiner—James B. Monroe
Attorney, Agent, or Firm—Armstrong, Nikaido, Marmelstein, Kubovcik & Murray

[57] ABSTRACT

A pigment material, the surfaces of which are treated with a saturated fatty acid triglyceride having an iodine value of not more than 5. The treated pigment material, which is used in cosmetics, has strong water repellency, feels smooth, and adheres well to the skin.

4 Claims, No Drawings

SURFACE-TREATED PIGMENT MATERIAL

BACKGROUND OF THE INVENTION

1. Field of the Invention

The present invention relates to a new surface-treated pigment material.

2. Description of the Prior Art

Makeup cosmetics such as powder foundations, rouges, and eye shadows are given water repellency for protection from perspiration so that they stay longer on the skin and in good condition. The object is achieved by adding a metallic soap to cosmetics, or by coating pigments with a silicone or metallic soap. Silicone-treated pigments have a very high degree of water repellency but are poor in adhesion to the skin. In addition, they tend to make the skin feel dry. On the other hand, metallic soap-treated pigments are good in adhesion, but are somewhat poor in spreadability and feel. In order to eliminate these disadvantages, there have been proposed a variety of substances for treating pigments.

Examples of such substances include animal oils such as squalene and lanolin, fatty acids such as myristic acid and stearic acid and esters thereof, vegetable oils such as olive oil and avocado oil, glycerol ester of coconut acid, natural waxes such as beeswax and Japan wax, and fats and oils.

Animal and vegetable oils, and fatty acids (such as myristic acid and stearic acid) and esters thereof are not so effective in improving the feeling of cosmetics. In addition, they are apt to deteriorate to give off an offensive odor when heated in the treatment process.

Natural fats and oils including Japan wax are somewhat effective in improving the feel of the cosmetics, but they become discolored or give off an offensive odor when heated. Because of these disadvantages, they are not suitable for cosmetics.

SUMMARY OF THE INVENTION

In order to solve the above-mentioned problems and to develop an improved pigment material for makeup cosmetics, the present inventors carried out extensive studies and, as a result, completed the present invention.

Accordingly, it is an object of the present invention to provide a surface-treated pigment material, which is characterized in that the surfaces of the pigment are substantially uniformly coated with a layer of triglyceride of a saturated fatty acid.

It is another object of the invention to provide a makeup cosmetic containing said pigment material.

The pigment material (which includes extender pigments) coated with a triglyceride of a saturated fatty acid according to this invention gives a smooth feel, spreads well, and adheres well to the skin. Also, the pigment material according to this invention which is simultaneously or consecutively with a triglyceride of a saturated fatty acid and a water repellent such as silicone and metallic soap has strong water repellency, feels smooth, spreads well, and adheres well to the skin.

The makeup cosmetics containing the surface-treated pigment material of this invention are by far superior in feeling, spreadability, adhesion, and smoothness to the conventional cosmetics containing a pigment treated with a silicone, metallic soap, or the like.

The saturated fatty acid triglyceride used in the invention is obtained by esterifying a saturated fatty acid with glycerol. It is also obtained by hydrogenating an unsaturated fatty acid triglyceride contained in natural fats and oils and waxes. It should have an iodine value of not more than 5. It is important that the natural fats and oils before hydrogenation be of good quality with no oxidation and discoloration.

The fatty acid of the triglyceride used in the invention should have more than 10, preferably more than 12 carbon atoms, so that the treated pigment material has good smoothness.

Examples of the natural fats and oils for hydrogenation include animal fats and oils such as herring oil, sardine oil, egg yolk oil, beef tallow, and lard; and vegetable fats and oils such as coconut oil, castor oil, tsubaki oil, peanut oil, olive oil, sesame oil, cottonseed oil, rape oil, soybean oil, and rice oil. Additional examples that can be used include triglycerides of fatty acids having more than 10 carbon atoms which, upon hydrogentation, have an iodine value of not more than 5. They may be used individually or in combination with one another.

The saturated fatty acid triglyceride should be added in an amount of 0.2 to 30% by weight of the pigment material to be treated, preferably 0.5 to 10%, and more preferably 1–5%. With an amount less than 0.2%, the resulting treated pigment material is not satisfactory in adhesion. With an amount greater than 30%, the saturated fatty acid triglyceride bleeds to adversely affect the feel of the cosmetic.

The hydrogenation of the unsaturated fatty acid triglyceride may be accomplished in the usual way with pressurized and heated hydrogen in the presence of a metal catalyst such as nickel.

The water repellent that can be used in the invention includes, for example, silicone oil, metallic soap, salt of acylamino acid, acylated peptide salt, and fluorine-based water repellent. They may be used individually or in combination with one another. The amount of the water repellent is 0.5 to 5% by weight of the pigment material to be treated.

The surface treatment of pigment materials with the saturated fatty acid triglyceride is carried out in the manner shown as an example in the following.

First, a saturated fatty acid triglyceride prepared as mentioned above is dissolved or dispersed in an organic solvent at normal temperature or with heating. An appropriate organic solvent is selected from alcohols, ethers, esters, ketones, paraffin hydrocarbons, methylene chloride, chloroform, and the like which do not degrade or hydrolyze the saturated fatty acid triglyceride.

Then, the resulting solution is thoroughly mixed with a pigment material to be treated. The pigment material includes inorganic pigments such at titanium oxide, zinc oxide, zirconium oxide, iron oxide red, iron oxide yellow, iron oxide black, ultramarine blue, iron blue, chromium oxide, and chromium hydroxide; and extender pigments such as mica (muscovite and sericite), magnesium carbonate, calcium carbonate, aluminum silicate, magnesium silicate, calcium silicate, and clay. The pigment material also includes Ti-mica, bismuth oxychloride, coal-tar dyes, natural dyes, silica beads, and plastics beads (beads of polyamide resin, acrylic resin, etc.). After mixing, the treated pigment material is dried. Thus there is obtained a pigment material coated with a saturated fatty acid triglyceride.

According to a preferred manner, the pigment material is made hydrophobic by treatment with a silicone oil, metallic soap, salt of acylamino acid, acylated peptide salt, fluorine-based water repellent, or the like, prior to or simultaneously with the treatment with a saturated fatty acid triglyceride.

The treated pigment material thus obtained is very smooth and spreadable, and is superior to the conventional silicone-treated pigment and metallic soap-treated pigment. Furthermore, the combined treatment with the saturated fatty acid triglyceride and a conventional water repellent provides a pigment material having superior characteristic properties.

On mixing with a makeup cosmetic, the treated pigment material imparts good smoothness, spreadability, and feel to the cosmetic.

DETAILED DESCRIPTION OF THE INVENTION

The invention is described in more detail with reference to the following examples, which are not intended to limit the scope of the invention.

EXAMPLE 1

100 g of talc (having an average particle diameter of 5 μm) was mixed with a solution containing 2 g of hydrogenated coconut oil (having an iodine value of 1.5) dissolved in 15 g of xylol, with stirring for 10 minutes by using a household mixer. Upon drying at 100° C. for 2 hours, there was obtained a treated powder, the surfaces of which were coated with a saturated fatty acid triglyceride. It was much smoother and more spreadable than untreated talc, and had an odor which was acceptable for use of cosmetics.

Comparative EXAMPLE 1

100 g of talc (having an average particle diameter of 5 μm) was mixed with a solution containing 2 g of coconut oil (having an iodine value of 10) dissolved in 15 g of xylol, with stirring for 10 minutes by using a household mixer. Upon drying at 100° C. for 2 hours, there was obtained a treated powder, the surfaces of which were coated with an unsaturated fatty acid triglyceride. It was much smoother and more spreadable than untreated talc, but had an odor that was unacceptable for use in cosmetics.

EXAMPLE 2

50 g of sericite was mixed with a solution containing 1 g of methylhydrogenpolysiloxane and 1 g of hydrogenated egg yolk oil (having an iodine value of 0.5) in 15 g of benzene, with stirring for 10 minutes by using a household mixer. The treated sericite was air-dried at room temperature to remove benzene completely, and then baked at 120° C. for 3 hours.

There was obtained a treated powder, the surfaces of which were coated with a silicone and a saturated fatty acid triglyceride.

Comparative EXAMPLE 2

100 g of sericite was uniformly dispersed into 0.5 liters of water with vigorous agitation. In the resulting dispersion was completely dissolved 1 g of potassium myristate. Then 10 ml of a 20% aqueous solution of zinc sulfate was added dropwise over 10 minutes. Further then, a solution containing 2 g of lanolin in 20 g of hot ethanol was added dropwise. Stirring was continued for 10 minutes. The product was filtered with suction using a Buchner funnel, followed by crushing and hot air drying at 105° C. for 10 hours.

There was obtained a treated powder, with the surfaces of which were coated with a metallic soap and lanolin.

Comparative EXAMPLE 3

1.5 g of methylhydrogenpolysiloxane was completely dissolved in 15 g of benzene, and the resulting solution was added to 50 g of sericite with mixing by a household mixer for 5 minutes. The resulting product was air-dried at room temperature to remove benzene completely, followed by baking at 120° C. for 3 hours.

There was obtained a treated powder, the surfaces of which were coated with silicone.

EXAMPLE 3

50 g of the silicone-treated sericite obtained in Comparative Example 3 was thoroughly mixed with a solution containing 1 g of stearic acid triglyceride in 10 g of ethyl ether, followed by air-drying.

There was obtained a treated powder, the surfaces of which were coated with a silicone and a saturated fatty acid triglyceride.

The powders obtained in the four preceding experiments were tested for adhesion, feel, and water repellency by the following methods.

Test Method 1

(Adhesion)

Equal amounts of powder are applied to frosted glass (5 cm×5 cm). 100 ml of water (cold) is poured over each coated glass. The amount of powder remaining on the glass is observed.

Test Method 2

(Feeling)

The powder is rubbed between the thumb and forefinger. An observation is made as to whether the powder feels soft, wet, or smooth. In each category, the powder is rated from one to ten, ten being best.

Test Method 3

(Water Repellency)

Into a 100 ml beaker containing 50 ml of water, 0.5 g of treated powder is added, followed by stirring with a glass rod fifty times. The water repellency is rated from one to ten. Completely clear water is equal to ten. All powder in suspension is equal to one.

The results are shown in Table 1.

TABLE 1

| | Adhesion | Feeling | | | Water Repellency |
| --- | --- | --- | --- | --- | --- |
| | | Soft | Wet | Smooth | |
| Example 2 | Approx. 80% | 10 | 10 | 10 | 10 |
| Comparative Example 2 | Approx. 70% | 6 | 6 | 4 | 6 |
| Comparative Example 3 | Approx. 5% | 4 | 4 | 6 | 10 |
| Example 3 | Approx. 70% | 8 | 8 | 8 | 10 |

What we claim:

1. A surface-treated pigment material consisting essentially of pigment material of which the surfaces are uniformly coated with a coating consisting essentially of a water repellent and at least one saturated fatty acid triglyceride, wherein the saturated fatty acid triglyceride has an iodine value of not more than 5 and is obtained by esterifying a saturated fatty acid having at least 12 carbon atoms or by hydrogenating a triglyceride of an unsaturated fatty acid having at least 12 carbon atoms, said triglyceride of an unsaturated fatty acid being found in natural fats, oils and waxes, and wherein the amount of saturated fatty acid triglyceride is 0.2 to 30% by weight based on the amount of pigment material to be treated.

2. A surface-treated pigment material as in claim 1, wherein the amount of saturated fatty acid triglyceride is 1 to 5% by weight based on the amount of pigment material to be treated.

3. A surface-treated pigment material as in claim 1, wherein the amount of the water repellent is 0.5 to 5% by weight based on the amount of pigment material to be treated.

4. A surface-treated pigment material as in claim 1, wherein the amount of saturated fatty acid triglyceride is 0.5 to 10% by weight based on the amount of pigment material to be treated.

* * * * *